United States Patent
Héja et al.

(10) Patent No.: US 6,600,039 B1
(45) Date of Patent: Jul. 29, 2003

(54) PROCESS FOR THE PREPARATION OF N-(1,1-DIMETHYLETHYL)-4-[[5'-ETHOXY-4-CIS[2-(4-MORPHOLINO)ETHOXY]-2'-OXOSPIRO[CYCLOHEXAN-1,3'[H]INDOL]1'(2'-H)-YL]-SULFONYL]-3-METHOXYBENZAMIDE AND ITS SALTS

(75) Inventors: Gergely Héja, Szentendre (HU); Éva Csikós, Budapest (HU); Tünde Erösné Takácsy, Budapest (HU); Csaba Gönczi, Budapest (HU); Judit Halász, Budapest (HU); István Hermecz, Budapest (HU); Csilla Majláth, Budapest (HU); Lajos Nagy, Szentendre (HU); Andrea Sántáné Csutor, Budapest (HU); Péter Sárosi, Budapest (HU); Kálmán Simon, Budapest (HU); Tiborné Szomor, Budapest (HU); Györgyné Szvoboda, Dunakeszi (HU)

(73) Assignee: Sanofi-Synthelabo, Paris (FR)

( * ) Notice: Subject to any disclaimer, the term of this patent is extended or adjusted under 35 U.S.C. 154(b) by 0 days.

(21) Appl. No.: 10/030,647

(22) PCT Filed: Jul. 13, 2000

(86) PCT No.: PCT/HU00/00078

§ 371 (c)(1),
(2), (4) Date: Apr. 17, 2002

(87) PCT Pub. No.: WO01/05791

PCT Pub. Date: Jan. 25, 2001

(30) Foreign Application Priority Data

Jul. 15, 1999 (HU) .............................................. 9902376

(51) Int. Cl.$^7$ .............................................. C07D 273/00
(52) U.S. Cl. ....................................................... 544/70
(58) Field of Search ............................................ 544/70

(56) References Cited

U.S. PATENT DOCUMENTS 5,994,350 A     11/1999    Foulon et al.
6,090,818 A  *   7/2000    Foulon et al. ............... 514/278

FOREIGN PATENT DOCUMENTS

FR     WO 98/25901    *   6/1998
WO    WO 97 15556 A      5/1997

OTHER PUBLICATIONS

Serradeil–Le C, Lacour C, Valette G, et al. Characterization of SR 121463A, a highly potent and selective, orally active vasopressin V2 receptor antagonist. J Clin Invest 1996; 98:2729–38.*

* cited by examiner

Primary Examiner—Deborah C. Lambkin
(74) Attorney, Agent, or Firm—Michael D. Alexander; Paul E. Dupont

(57) ABSTRACT

The invention relates to a process for the preparation of a compound of formula (I) and the salts thereof by reacting the compound of formula (II) with the compound of formula (III), which comprises carrying out the reaction in dimethyl sulfoxide, at a temperature between 10° C. and 40° C., preferably at room temperature and transforming the resulting base of formula (I), if desired, into its salt by a method known per se.

2 Claims, No Drawings

PROCESS FOR THE PREPARATION OF N-(1,1-DIMETHYLETHYL)-4-[[5'-ETHOXY-4-CIS[2-(4-MORPHOLINO)ETHOXY]-2'-OXOSPIRO[CYCLOHEXAN-1,3'[H]INDOL]1'(2'-H)-YL]-SULFONYL]-3-METHOXYBENZAMIDE AND ITS SALTS

The subject of the present invention is a process for the preparation of N-(1,1-dimethylethyl)-4-[[5'-ethoxy-4-cis-[2-(4-morpholino)ethoxy]-2'-oxospiro[cyclohexan- 1,3'-[3H]indol]-1'(2'H)-yl]-sulfonyl]-3-methoxybenzamide (SR 121463) of formula I

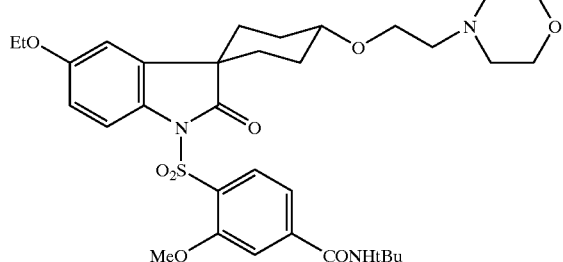

and its salts, compounds having vasopressine $V_2$ antagonistic effect.

According to patent application WO 9715556 the compound of formula I is prepared by reacting the spiro/cis-4-(beta-morpholino-ethyloxy)cyclohexan-1,3'-(5'-ethoxy)-[3H]indol-2'[1'H]one of formula II

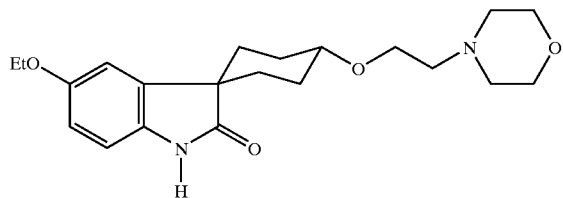

with the 2-methoxy-4-(N-t-butylaminocarbonyl)benzenesulfonyl chloride of formula III

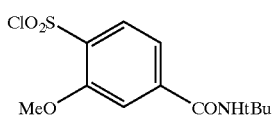

using potassium-t-butylate in tetrahydrofuran.

Because of the applied solvent (tetrahydrofuran) and reaction temperature (between –60° C. and 40° C.) it is not easy to carry out the process under industrial conditions, the yield is low, the product is contaminated, its purification requires repeated crystallization.

To our surprise, we have found that by stirring in dimethyl sulfoxide at room temperature the reaction proceeds in very good yield (85–92%). The work-up procedure is simple, while in the original process the product is obtained by extraction, in the present process the base precipitates on diluting the reaction mixture with water, and it can be filtered off. The purity of the resulting base is 93–96% and the salt formed from it is appropriately pure.

In accordance with the above, the subject of the invention is a process for the, preparation of the compound of the formula I

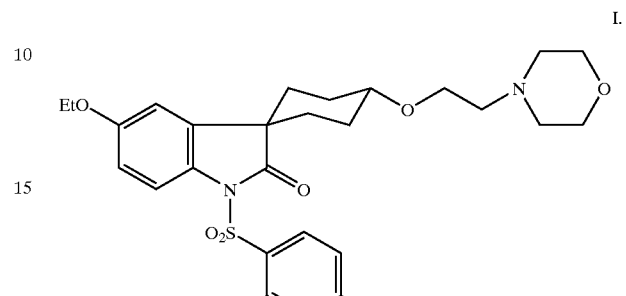

and the salts thereof, by reacting the compounds of the formula II

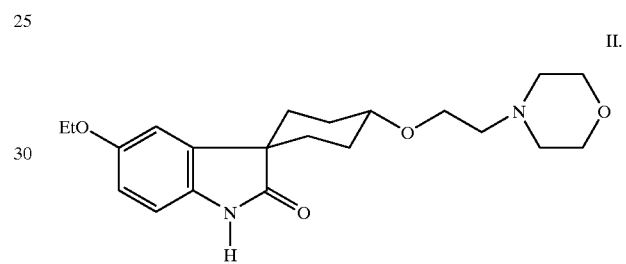

and III,

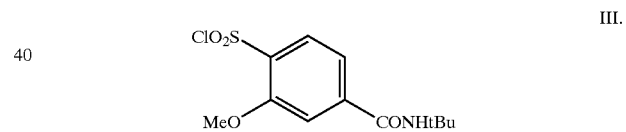

which comprises carrying out the reaction in dimethyl sulfoxide at a temperature between 10° C. and 40° C., preferably at room temperature and transforming the resulting base of formula I into its salt by a method known per se.

The process according to the invention is illustrated by the following examples:

EXAMPLE 1

In 180 ml of dimethyl sulfoxide 26.7 g of potassium t-butylate is dissolved. After 10 minutes of stirring 74.9 g of compound II is added to the mixture, at 20–25° C., and the mixture is stirred until complete dissolution. Then rapidly, keeping the temperature below 25° C., the compound of formula III is added to the mixture. The resulting light-brown suspension is stirred at 25° C. for 1.5 hours, then it is decomposed with 700 ml of ice-water. After 1 hour of stirring, the precipitate is filtered off, suspended and washed with 2×500 ml of water, thoroughly sucked and washed with 2×100 ml of 96% ethanol. 117 g of compound of formula I is obtained, assay (by HPLC): 95.2% Yield: 90.8%.

EXAMPLE 2

1 mol of the base of compound I is suspended in 3–5-fold amount of ethanol and to the mixture 0.5–1 mol of acid is added. After dissolution the solution is clarified by active carbon and filtered. On cooling the salt precipitates, it is filtered off, washed with a small amount of cold ethanol and dried. Yield ranges between 87–95%. Dihydrogenphosphate monohydrate salt: mp.: 164.5° C.

| | |
|---|---|
| Hydrogen maleate salt | mp.: 184–185° C. |
| Hydrogen fumarate salt | mp.: 182–183° C. |

What we claim is:

1. A process for the preparation of a compound of formula I

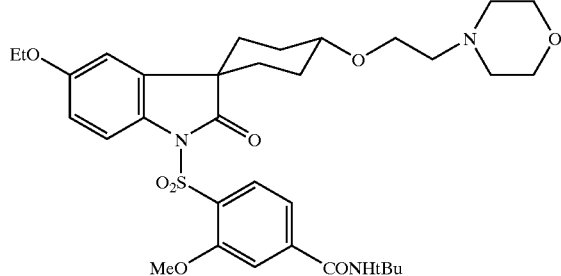

I.

and the salts thereof by reacting the compound of formula II

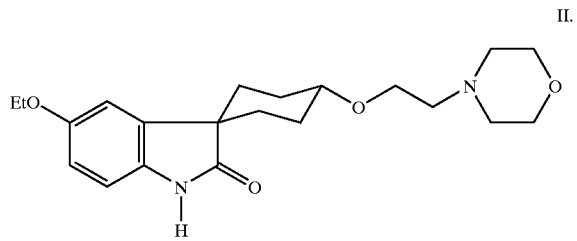

II.

with the compound of formula III,

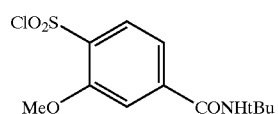

III.

which comprises carrying out the reaction in dimethyl sulfoxide in the presence of potassium-t-butylate, at a temperature between 10° C. and 40° C., and transforming the resulting base of formula I, if desired, into a pharmaceutically acceptable salt thereof by treatment with an acid.

2. A process according to claim 1 which comprises carrying out the reaction at room temperature.

* * * * *